United States Patent [19]

Böhner et al.

[11] 3,966,754
[45] June 29, 1976

[54] CERTAIN SULFONIC ACID ESTERS

[75] Inventors: Beat Böhner, Binningen; Dag Dawes, Pratteln; Willy Meyer, Basel; Haukur Kristinsson, Bottmingen; Kurt Rüfenacht, Basel, all of Switzerland

[73] Assignee: Ciba-Geigy Corporation, Ardsley, N.Y.

[22] Filed: June 12, 1974

[21] Appl. No.: 478,680

[30] Foreign Application Priority Data
June 14, 1973 Switzerland.......................... 8520/73
Apr. 29, 1974 Switzerland.......................... 5829/74

[52] U.S. Cl. .................... 260/308 R; 260/247.1 M; 260/302 D; 260/306.8 F; 260/307 G; 260/308 A; 260/308 B; 424/248; 424/269; 424/270; 424/272
[51] Int. Cl.²............... C07D 249/04; C07D 249/12
[58] Field of Search ........ 260/308 B, 308 R, 308 A

[56] References Cited
UNITED STATES PATENTS
2,849,352  8/1958  Kirstahler et al. .............. 260/308 R
2,943,017  6/1960  Sasse et al. ...................... 260/308 B OTHER PUBLICATIONS
Schrader, Chem. Abstracts, 54: 14271g (1955).

*Primary Examiner*—R. Gallagher
*Attorney, Agent, or Firm*—Harry Falber; Frederick H. Rabin

[57] ABSTRACT
Sulfonic acid esters of the formula

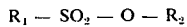

$$R_1 - SO_2 - O - R_2$$

wherein
  $R_1$ represents alkyl or alkenyl, and
  $R_2$ represents an unsubstituted or substituted heteroaromatic five-membered ring having three herero atoms, processes for their manufacture, and their use in pest control.

11 Claims, No Drawings

CERTAIN SULFONIC ACID ESTERS

The present invention relates to sulphonic acid esters, to processes for their preparation, and to their use in pest control.

The said sulphonic acid esters have the formula $$R_1-SO_2-O-R_2 \qquad (I)$$

wherein
$R_1$ represents alkyl or alkenyl, and
$R_2$ represents an unsubstituted or substituted heteroaromatic five-membered ring having three hetero atoms.

The alkyl and alkenyl groups denoted by $R_1$ can be branched-chain or straight-chain, unsubstituted, or substituted by, for example, halogen atoms, such as fluorine, chlorine, bromine and/or iodine, and/or by alkoxy or alkylthio groups, and they contain 1 to 18 and 2 to 18 carbon atoms, respectively, preferably, however, 1 to 6 and 2 to 5 carbon atoms, respectively. Examples of such groups are, inter alia: methyl, chloromethyl, trifluoromethyl, methoxymethyl, ethyl, ethoxyethyl, 2-chloroethyl, propyl, 3-chloropropyl, isopropyl, n-, i-, sec.-, tert.-butyl, n-pentyl, n-hexyl and isomers thereof, vinyl, propenyl and 3,3,3-trichloropropenyl.

Hetero atoms of the aromatic five-membered ring denoted by $R_2$, which itself can be part of a polynuclear, optionally also heterocyclic, ring system, are preferably oxygen, sulphur, nitrogen and/or

and substituents are preferably halogen atoms, such as fluorine, chlorine, bromine and/or iodine, alkyl, alkoxy, alkylthio, alkylsulphinyl, alkylsulphonyl, alkylthioalkyl, haloalkyl, alkoxyalkyl, alkenyl, alkenyloxy, alkenylthio, alkynyl, alkynyloxy, alkynylthio, amino, monoalkylamino, dialkylamino, carbamoyl, phenyl, phenylthio, phenylsulphinyl, phenylsulphonyl, benzyl, benzylthio, benzylsulphinyl, benzylsulphonyl, 1-phenethyl, 2-phenethyl, diphenylmethyl, carbalkoxy, cycloalkyl, nitro or cyano groups. The phenyl, phenylthio, phenylsulphinyl, phenylsulphonyl, benzyl, 1-phenethyl, 2-phenethyl, diphenylmethyl, and cycloalkyl groups can also be optionally mono- or polysubstituted, identically or differently, e.g. by halogen atoms such as fluorine, chlorine, bromine and/or iodine, alkyl, haloalkyl, alkoxy, alkylthio and/or nitro groups.

Examples of such heteroaromatic five-membered-ring groups having three hetero atoms are, inter alia:

| | |
|---|---|
| 1,2,3-triazolyl(4), | 1,2,3-triazolyl(5), |
| 1,2,4-triazolyl(3), | 1,2,4-triazolyl(5) |
| 2,4-oxadiazolyl(3), | 1,2,4-oxadiazolyl(5), |
| 1,2,4-thiadiazolyl(3), | 1,2,4-thiadiazolyl(5) |
| 1,2,5-oxadiazolyl(3), | 1,3,4-oxadiazolyl(2), |
| 1,2,3-benztriazolyl(3), | 1-oxy-1,2,3-triazolyl(4), |
| 1,2,4-triazolo-(2,3b)-thiazolyl(6), | |
| 1,2,5-thiadiazolyl(3). | |

Compounds of formula I preferred by virtue of their action are those wherein
$R_1$ represents optionally substituted $C_1-C_6$-alkyl or $C_2-C_5$-alkenyl, and
$R_2$ represents optionally substituted 1,2,3-triazolyl(4),

| | |
|---|---|
| 1,2,3-triazolyl(5), | 1,2,4-triazolyl(3), |
| 1,2,4-triazolyl(5), | 1,2,4-oxadiazolyl(3), |
| 1,2,4-oxadiazolyl(5), | 1,2,4-thiadiazolyl(3), |
| 1,2,4-thiadiazolyl(5), | 1,2,5-oxadiazolyl(3), |
| 1,3,4-oxadiazolyl(2), | 1,2,3-benztriazolyl(3), |
| 1-oxy-1,2,3-triazolyl(4), | 1,2,5-thiadiazolyl(3), or |
| 1,2,4-triazolo-(2,3b)-thiazolyl(6). | |

Particularly preferred compounds of formula I, however, are those wherein
$R_1$ represents unsubstituted $C_1-C_6$-alkyl, $C_1-C_6$-alkyl substituted by fluorine or chlorine, or 3,3,3-trichloropropenyl(1), and
$R_2$ represents optionally substituted 1,2,4-triazolyl(3) or 1,2,4-oxadiazolyl(3).

The compounds of formula I are prepared according to known methods; for example, as follows:

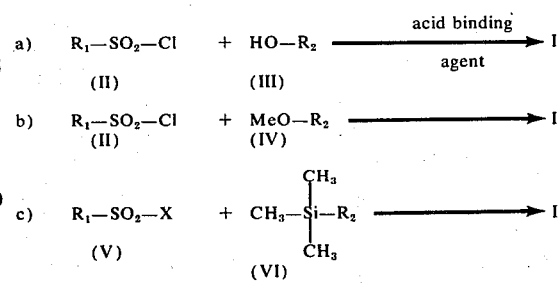

In formulae II to VI, the symbols $R_1$ and $R_2$ have the meanings given for formula I, X stands for halogen, particularly for fluorine or chlorine, and Me for a metal, especially an alkali metal, ammonium or alkylammonium. Suitable acid-binding agents are: tertiary amines, e.g. trialkylamines, pyridine or dialkylaniline; inorganic bases such as hydrides or hydroxides; or carbonates and bicarbonates of alkali metals and alkaline-earth metals.

The processes (a), (b) and (c) are performed at a reaction temperature of −2°–150°C, at normal pressure, as well as, in the case of process c), at elevated pressure, and in solvents or diluents.

Suitable solvents or diluents are, for example, ethers and ethereal compounds, such as diethyl ether, dipropyl ether, dioxane or tetrahydrofuran; amides such as N,N-dialkylated carboxylic acid amides; aliphatic, aromatic as well as halogenated hydrocarbons, particularly benzene, toluene, xylenes, chloroform or chlorobenzene; nitriles such as acetonitrile; ketones such as acetone or methyl ethyl ketone; and water or mixtures thereof.

The starting materials of formulae II, III, IV, V and VI are known, or can be prepared by methods analogous to known methods.

The compounds of formula I have a broad biocidal action, and can be used for the control of various animal and plant pests.

They are particularly suitable for the control of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae; as well as acarids of the families: Ixodidae, Argasidae, Tetranychidae and Dermanyssidae.

The insecticidal or acaricidal action can be appreciably broadened and adapted to suit given circumstances by the addition of other insecticides and/or acaricides. Suitable additives are, for example, the following active substances:

organic phosphorus compounds,
nitrophenols and derivatives thereof,
pyrethrin-like compounds,
formamidines,
ureas, carbamates, and
chlorinated hydrocarbons.

In addition to possessing the above-mentioned properties, the compounds of formula I are effective also against members of the division Thallophyta. Some of these compounds thus have a bactericidal action. In particular, however, they are effective against fungi, especially against phytopathogenic fungi belonging to the following classes: Oomycetes, Zygomycetes, Ascomycetes, Basidiomycetes and Denteromycetes. The compounds of formula I moreover have a fungitoxic action in the case of fungi which attack the plants from the soil. Furthermore, the new active substances are suitable for the treatment of seed, fruits, tubers, etc., for protection against fungus infections. The compounds of formula I are suitable also for the control of phytopathogenic nematodes.

The compounds of formula I can be used on their own or together with suitable carriers and/or additives. Suitable carriers and additives may be solid or liquid, and they correspond to the substances common in formulation practice, such as, e.g. natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice. Also to be mentioned are cattle dips and spray races, in which aqueous preparations are used.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

solid preparations:
dusts, scattering agents, granulates, coated granulates, impregnated granulates and homogeneous granulates;

liquid preparations:
a. water-dispersible active-substance concentrates: wettable powders, pastes or emulsions;
b. solutions.

The content of active substance in the described agents is between 0.1 and 95%.

The active substances of formula I can be formulated, for example, as follows:

Dusts:
The following substances are used in the preparation of (a) a 5% dust, and (b) a 2% dust:

(a)
5 parts of active substance,
95 parts of talcum;

(b)
2 parts of active substance,
1 part of highly dispersed silicic acid,
97 parts of talcum.

The active substances are mixed and ground with the carriers.

Granulate:
The following substances are used to prepare a 5% granulate:
5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone subsequently evaporated off in vacuo.

Wettable powder:
The following constituents are used for the preparation of (a) a 40%, (b) and (c) a 25%, and (d) a 10% wettable powder;

(a)
40 parts of active substance,
5 parts of sodium lignin sulphonate,
1 part of sodium dibutyl-naphthalene sulphonate,
54 parts of silicic acid;

(b)
25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

(c)
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to prepare (a) a 10% and (b) a 25% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)

25 parts of active substance,
2.5 parts of epoxidised vegetable oil,
10 parts of an alkylarylsulphonate/fatty alcohol polyglycol ether mixture,
5 parts of dimethylformamide,
57.5 parts of xylene.

From these concentrates it is possible to prepare, by dilution with water, emulsions of any desired concentration.

Spray:

The following constituents are used to prepare a 5% spray:
5 parts of active substance,
1 part of epichlorhydrin,
94 parts of ligroin (boiling limits 160°–190°C).

EXAMPLE 1

Preparation of 1-isopropyl-1,2,4-triazolyl-(3)-methanesulphonic acid ester 29.4 g of 1-isopropyl-3-hydroxy-1,2,4-triazole and 27.6 g of potassium carbonate are refluxed in 500 ml of methyl ethyl ketone for 2 hours. After the dropwise addition of 22.9 g of methanesulphonic acid chloride at room temperature, the mixture is again refluxed this time for 1 hour and subsequently cooled. The insoluble salts are filtered off; the clear filtrate is concentrated in vacuo, the residue is suspended in absolute ether, the insoluble constituents are filtered off and concentration in vacuo is again performed. There is obtained the compound of the formula

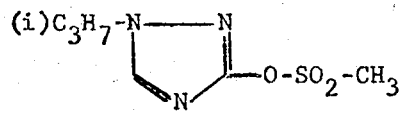

in the form of clear yellow-orange oil having a refractive index of $n_D^{20} = 1.4736$.

The following compounds can be prepared in an analogous manner:

| Heterocycles | Sulphonic acid halide | Product | Physical data |
| --- | --- | --- | --- |
| 1-ethyl-3-hydroxy-5-chloro-1,2,4-triazole | methanesulphonic acid chloride | 1-ethyl-5-chloro-1,2,4-triazolyl-(3)-methanesulphonate | $n_D^{20}=1.4871$ |
| 1-(1-phenylethyl)-3-hydroxy-5-chloro-1,2,4-triazole | methanesulphonic acid chloride | 1-(1-phenylethyl)-5-chloro-1,2,4-triazolyl-(3)-methanesulphonate | $n_D^{20}=1.5363$ |
| 1-ethyl-3-hydroxy-5-methyl-1,2,4-triazole | methanesulphonic acid chloride | 1-ethyl-5-methyl-1,2,4-triazolyl-(3)-methanesulphonate | $n_D^{20}=1.4771$ |
| 1-diphenylmethyl-3-hydroxy-1,2,4-triazole | methanesulphonic acid chloride | 1-diphenylmethyl-1,2,4-triazolyl-(3)-methanesulphonate | M.P. 80–82°C |
| 1-isopropyl-3-hydroxy-5-dimethylamino-1,2,4-triazole | methanesulphonic acid chloride | 1-isopropyl-5-dimethylamino-1,2,4-triazolyl-(3)-methanesulphonate | $n_D^{20}=1.4792$ |
| 1-phenyl-3-hydroxy-5-dimethylcarbamoyl-1,2,4-triazole | methanesulphonic acid chloride | 1-phenyl-5-dimethylcarbamoyl-1,2,4-triazolyl-(3)-methanesulphonate | M.P. 80–89°C |
| 1-ethyl-3-hydroxy-1,2,4-triazole | methanesulphonic acid chloride | 1-ethyl-1,2,4-triazolyl-(3)-methanesulphonate | M.P. 33–35°C |
| 1-isopropyl-3-hydroxy-1,2,4-triazole | isopropanesulphonic acid chloride | 1-isopropyl-1,2,4-triazolyl-(3)-isopropanesulphonate | $n_D^{20}=1.4716$ |
| 1-isopropyl-3-hydroxy-1,2,4-triazole | n-butanesulphonic acid chloride | 1-isopropyl-1,2,4-triazolyl-(3)-iso-n-butanesulphonate | $n_D^{20}=1.4729$ |
| 2-(4-chlorophenyl)-4-hydroxy-1,2,3-triazole | methanesulphonic acid chloride | 2-(4-chlorophenyl)-1,2,3-triazolyl-(4)-methanesulphonate | M.P. 114°C |
| 2-phenyl-4-hydroxy-1,2,3-triazole | methanesulphonic acid chloride | 2-phenyl-1,2,3-triazolyl-(4)-methanesulphonate | M.P. 85° C |
| 1-oxy-2-(4-chlorophenyl)-4-hydroxy-1,2,3-triazole | methanesulphonic acid chloride | 1-oxy-2-(4-chlorophenyl)-1,2,3-triazolyl-(4)-methanesulphonate | M.P. 157°C |
| 1-phenyl-3-hydroxy-1,2,4-triazole | methansulphonic acid chloride | 1-phenyl-1,2,4-triazolyl-(3) methanesulphonate | M.P. 83–85°C |
| 1-phenyl-3-hydroxy-5-methylthio-1,2,4-triazole | methanesulphonic acid chloride | 1-phenyl-5-methylthio-1,2,4-triazolyl-(3)-methanesulphonate | $n_D^{20}=1.5804$ |
| 1-phenyl-3-hydroxy-5-ethylthio-1,2,4-triazole | methanesulphonic acid chloride | 1-phenyl-5-ethylthio-1,2,4-triazolyl-(3)-methansulphonate | $n_D^{20}=1.5708$ |
| 1-cyanoethyl-3-hydroxy-5-methyl-1,2,4-triazole | methanesulphonic acid chloride | 1-cyanoethyl-5-methyl-1,2,4-triazolyl-(3)-methanesulphonate | M.P. 76–78°C |

| Heterocycles | Sulphonic acid halide | Product | Physical data |
|---|---|---|---|
| 1-(4'-chlorophenyl)-3-hydroxy-5-methyl-1,2,4-triazole | methanesulphonic acid chloride | 1-(4-chlorophenyl)-5-methyl-1,2,4-triazolyl-(3)methanesulphonate | M.P. 119–122°C |
| 1-cyanoethyl-3-hydroxy-1,2,4-triazole | methanesulphonic acid chloride | 1-cyanoethyl-1,2,4-triazolyl-(3)methane sulphonate | M.P. 65–68°C |
| 1-methyl-3-hydroxy-5-n-hexylthio-1,2,4-triazole | methanesulphonic acid chloride | 1-methyl-5-n-hexylthio-1,2,4-triazolyl-(3)-methanesulphonate | $n_D^{20}=1.5008$ |
| 1-methyl-3-ydroxy-5-(1-phenylethyl)-thio-1,2,4-triazole | methanesulphonic acid chloride | 1-methyl-5-(1-phenylethyl)thio-1,2,4-triazolyl-(3)-methanesulphonate | $n_D^{20}=1.5559$ |
| 1-methyl-3-hydroxy-5-(4-chloro-2-butenyl)-thio-1,2,4-triazole | methanesulphonic acid chloride | 1-methyl-5-(4-chloro-2-butenyl)thio-1,2,4-triazolyl-(3)-methanesulphonate | $n_D^{20}=1.5394$ |
| 1-n-propyl-3-hydroxy-1,2,4-triazole | methanesulphonic acid chloride | 1-propyl-1,2,4-triazolyl-(3)-methanesulphonate | $n_D^{20}=1.4761$ |
| 1-n-butyl-3-hydroxy-1,2,4-triazole | methanesulphonic acid chloride | 1-n-butyl-1,2,4-triazolyl-(3)-methanesulphonate | $n_D^{20}=1.4750$ |
| 1-ethyl-5-methyl-3-hydroxy-1,2,4-triazole | methanesulphonic acid chloride | 1-ethyl-5-methyl-1,2,4-triazolyl-(3)-methanesulphonate | $n_D^{20}=1.4771$ |
| 1-isopropyl-3-hydroxy-5-methyl-1,2,4-triazole | methanesulphonic acid chloride | 1-isopropyl-5-methyl-1,2,4-triazolyl-(3)-methanesulphonate | M.P.= 4.5–9°C |
| 1-propyl-3-hydroxy-5-chloro-1,2,4-triazole | methanesulphonic acid chloride | 1-propyl-5-chloro-1,2,4-triazolyl-(3)-methanesulphonate | $n_D^{20}=1.4789$ |
| 1-isopropyl-3-hydroxy-5-chloro-1,2,4-triazole | methanesulphonic acid chloride | 1-isopropyl-5-chloro-1,2,4-triazoll-(3)-methanesulphonate | $n_D^{20}=1.4808$ |
| 1-sec.-butyl-3-hydroxy-5-chloro-1,2,4-triazole | methanesulphonic acid chloride | 1-sec.-butyl-5-chloro-1,2,4-triazolyl-(3)-methanesulphonate | $n_D^{20}=1.4785$ |
| 1-neo-hexyl-3-hydroxy-5-chloro-1,2,4-triazole | methanesulphonic acid chloride | 1-neo-hexyl-5-chloro-1,2,4-triazolyl-(3)-methanesulphonate | M.P. 122–124°C |
| 1-methyl-3-hydroxy-5-methylthio-1,2,4-triazole | methanesulphonic acid chloride | 1-methyl-5-methylthio-1,2,4-triazolyl-(3)-methanesulphonate | $n_D^{20}=1.5249$ |
| 1-methyl-3-hydroxy-5-propylthio-1,2,4-triazole | methanesulphonic acid chloride | 1-methyl-5-propylthio-1,2,4-triazolyl-(3)-methanesulphonate | $n_D^{20}=1.5106$ |
| 1-methyl-3-hydroxy-5-isopropylthio-1,2,4-triazole | methanesulphonic acid chloride | 1-methyl-5-isopropyl-thio-1,2,4-triazolyl-(3)-methanesulphonate | $n_D^{20}=1.5087$ |
| 1-methyl-3-hydroxy-5-isobutylthio-1,2,4-triazole | methanesulphonic acid chloride | 1-methyl-5-isobutyl-thio-1,2,4-triazolyl-(3)-methanesulphonate | $n_D^{20}=1.5035$ |
| 1-methyl-3-hydroxy-5-n-pentylthio-1,2,4-triazole | methanesulphonic acid chloride | 1-methyl-5-n-pentyl-thio-1,2,4-triazolyl-(3)-methanesulphonate | $n_D^{20}=1.5051$ |
| 1-methyl-3-hydroxy-5-allylthio-1,2,4-triazole | chloromethyl-sulphonic acid chloride | 1-methyl-5-allylthio-1,2,4-triazolyl-(3) methyl chloride sulphonate | $n_D^{20}=1.5304$ |
| 1-methyl-3-hydroxy-5-(2-butenyl)-thio-1,2,4-triazole | methanesulphonic acid chloride | 1-methyl-5-(2-butenyl)-thio-1,2,4-triazolyl-(3)-methanesulphonate | $n_D^{20}=1.5261$ |
| 1-methyl-3-hydroxy-5-methylthioethylthio-1,2,4-triazole | methanesulphonic acid chloride | 1-methyl-5-methylthio-ethylthio-1,2,4-triazolyl-(3)-methanesulphonate | $n_D^{20}=1.5389$ |
| 1-methyl-3-hydroxy-5-(m-methylbenzyl)-thio-1,2,4-triazole | methanesulphonic acid chloride | 1-methyl-5-(m-methylbenzyl)-thio-1,2,4-triazolyl-(3)-methanesulphonate | $n_D^{20}=1.5603$ |
| 1-methyl-3-hydroxy-5-cyanomethylthio-1,2,4-triazole | methanesulphonic acid chloride | 1-methyl-5-cyanomethyl-thio-1,2,4-triazolyl-(3)-methanesulphonate | M.P. 82–83°C |
| 1-methyl-3-hydroxy-5-methallylthio-1,2,4-triazole | methanesulphonic acid cloride | 1-methyl-5-methallyl-thio-1,2,4-triazolyl-(3)-methanesulphonate | $n_D^{20}=1.5220$ |
| 1-methyl-3-hydroxy-5-(m-fluorobenzyl)-thio-1,2,4-triazole | methanesulphonic acid chloride | 1-methyl-5-(m-fluorobenzyl-thio-1,2,4-triazolyl-(3)-methanesulphonate | $n_D^{20}=1.5504$ |
| 1-methyl-3-hydroxy-5-(m-nitrobenzyl)-thio-1,2,4-triazole | methanesulphonic acid chloride | 1-methyl-5-(m-nitrobenzyl)-thio-1,2,4-triazolyl-(3)-methanesulphonate | $n_D^{20}=1.5801$ |
| 1-methyl-3-hydroxy-5-(m,p-dichlorobenzyl)-thio-1,2,4-triazole | methanesulphonic acid chloride | 1-methyl-5-(m,p-dichlorobenzyl)-thio-1,2,4-triazolyl-(3)-methanesulphonate | M.P. 82–83°C |
| 1-methyl-3-hydroxy-5-allylthio-1,2,4- | methanesulphonic acid chloride | 1-methyl-5-allylthio-1,2,4-triazolyl-(3)- | $n_D^{20}=1.5221$ |

-continued

| Heterocycles | Sulphonic acid halide | Product | Physical data |
|---|---|---|---|
| triazole | | methanesulphonate | |
| 1-methyl-3-hydroxy-5-dodecylthio-1,2,4-triazole | methanesulphonic acid chloride | 1-methyl-5-dodecylthio-1,2,4-triazolyl-(3)-methanesulphonate | M.P. 43–44°C |
| 1-ethyl-3-hydroxy-5-methylthio-1,2,4-triazole | methanesulphonic acid chloride | 1-ethyl-5-methylthio-1,2,4-triazolyl-(3)-methanesulphonate | $n_D^{20}=1.1529$ |
| 1-ethyl-3-hydroxy-5-ethylthio-1,2,4-triazole | methanesulphonic acid chloride | 1-ethyl-5-ethylthio-1,2,4-triazolyl-(3)-methanesulphonate | $n_D^{20}=1.5054$ |
| 1-n-propyl-3-hydroxy-5-methylthio-1,2,4-triazole | methanesulphonic acid chloride | 1-propyl-5-methylthio-1,2,4-triazolyl-(3)-methanesulphonate | $n_D^{20}=1.5086$ |
| 1-methyl-3-hydroxy-5-o-methylbenzylthio-1,2,4-triazole | methanesulphonic acid chloride | 1-methyl-5-o-methylbenzylthio-1,2,4-triazolyl-(3)-methanesulphonate | $n_D^{20}=1.5629$ |
| 1-isopropyl-3-hydroxy-5-ethylthio-1,2,4-triazole | methanesulphonic acid chloride | 1-ispropyl-5-ethylthio-1,2,4-triazolyl-(3)-methanesulphonate | $n_D^{20}=1.5002$ |
| 1-n-butyl-3-hydroxy-5-methylthio-1,2,4-triazole | methanesulphonic acid chloride | 1-n-butyl-5-methylthio-1,2,4-triazolyl-(3)-methanesulphonate | $n_D^{20}=1.5062$ |
| 1-isopropyl-3-hydroxy-5-methylsulphonylthio-1,2,4-triazole | methanesulphonic acid chloride | 1-isopropyl-5-methylsulphonylthio-1,2,4-triazolyl-(3)-methanesulphonate | M.P. 102–104° |
| 1-methylsulphonyl-3-hydroxy-5-ethyl-1,2,4-triazole | methanesulphonic acid chloride | 1-methylsulphonyl-5-ethyl-1,2,4-triazolyl-(3)-methanesulphonate | M.P. 156–158°C |
| 1-isopropyl-3-hydroxy-5-dimethylamino-1,2,4-triazole | methanesulphonic acid chloride | 1-isopropyl-5-dimethylamino-1,2,4-triazolyl-(3)-methanesulphonate | $n_D^{20}=1.4792$ |
| 1-methyl-3-hydroxy-5-p-bromobenzylthio-1,2,4-triazole | methanesulphonic acid chloride | 1-methyl-5-p-bromobenzylthio-1,2,4-triazolyl-(3)-methanesulphonate | M.P. 65–71°C |
| 1-methyl-3-hydroxy-5-o,o-dichlorobenzylthio-1,2,4-triazole | methanesulphonic acid chloride | 1-methyl-5-o-o-dichlorobenzylthio-1,2,4-triazolyl-(3)-methanesulphonate | M.P. 90–92°C |
| 1-diphenylmethyl-3-hydroxy-1,2,4-triazole | methanesulphonic acid chloride | 1-diphenylmethyl-1,2,4-triazolyl-(3)-methanesulphonate | M.P. 80–82°C |
| 1-phenyl-5-dimethylcarbamoyl-3-hydroxy-1,2,4-triazole | methanesulphonic acid chloride | 1-phenyl-5-dimethylcarbamoyl-1,2,4-triazolyl-(3)-methanesulphonate | M.P. 80–89°C |
| 1-(1-phenethyl)-3-hydroxy-1,2,4-triazole | methanesulphonic acid chloride | 1-(1-phenethyl)-1,2,4-triazolyl-(3)-methanesulphonate | semi-solid M.P.= 20–25°C |
| 1-(m-trifluoromethylphenyl)-3-hydroxy-1,2,4-triazole | methanesulphonic acid chloride | 1-(m-trifluoromethylphenyl)-1,2,4-triazolyl-(3)-methanesulphonate | M.P. 72–73°C |
| 1-(o-chlorophenyl)-3-hydroxy-1,2,4-triazole | methanesulphonic acid chloride | 1-(o-chlorophenyl)-1,2,4-triazolyl-(3)-methanesulphonate | M.P. 111–114°C |
| 1-(3'-chlorophenyl)-5-methyl-3-hydroxy-1,2,4-triazole | methanesulphonic acid chloride | 1-(3'-chlorophenyl)-5-methyl-1,2,4-triazolyl-(3)-methanesulphonate | M.P. 59–61°C |
| 3-methyl-6-hydroxy-1,2,4-triazolo-(2,3-b)-thiazole | methanesulphonic acid chloride | 3-methyl-1,2,4-triazolo-(2,3-b)-thiazolyl-(6)-methanesulphonate | M.P. 83–85°C |
| 5-isopropyl-3-hydroxy-1,2,4-oxadiazole | methanesulphonic acid chloride | 5-isopropyl-1,2,4-oxadiazolyl-(3)-methanesulphonate | $n_D^{20}=1.4558$ |
| 5-phenyl-3-hydroxy-1,2,4-thiadiazole | methanesulphonic acid chloride | 5-phenyl-1,2,4-thiadiazolyl-(3)-methanesulphonate | M.P. 90°C |
| 5-isopropyl-5-hydroxy-1,2,4-thiadiazole | methanesulphonic acid chloride | 5-isopropyl-1,2,4-thiadiazolyl-(3)-methanesulphonate | $n_D^{20}=1.5008$ |
| 1-isopropyl-3-hydroxy-1,2,4-triazole | 3,3,3-trichloropropenesulphonic acid chloride | 1-isopropyl-1,2,4-triazolyl-(3)-3',3',3'-trichloropropenesulphonate | $n_D^{20}=1.5129$ |
| 1-sec.-butyl-5-chloro-3-hydroxy-1,2,4-triazole | 3,3,3-trichloropropenesulphonic acid chloride | 1-sec.-butyl-5-chloro-1,2,4-triazolyl-(3)-3',3',3'-trichloropropeneslphonate | $n_D^{20}=1.5124$ |
| 1-sec.-butyl-3-hydroxy-1,2,4-triazole | methanesulphonic acid chloride | 1-sec.-butyl-1,2,4-triazolyl-(3)-methanesulphonate | |
| 1-i-butyl-3-hydroxy-1,2,4-triazole | methanesulphonic acid chloride | 1-i-butyl-1,2,4-triazolyl-(3)-methanesulphonate | |
| 1-sec.-pentyl-3-hydroxy-1,2,4-triazole | methanesulphonic acid chloride | 1-sec.-pentyl-1,2,4-triazolyl-(3)-methanesulphonate | |
| 1-n-hexyl-3-hydroxy-1,2,4-triazole | methanesulphonic acid chloride | 1-n-hexyl-1,2,4-triazolyl-(3)-methane- | |

-continued

| Heterocycles | Sulphonic acid halide | Product | Physical data |
|---|---|---|---|
| 1-sec.-hexyl-3-hydroxy-1,2,4-triazole | methanesulphonic acid chloride | 1-sec.-hexl-1,2,4-triazolyl-(3)-methanesulphonate | |
| 1-neo-hexyl-3-hydroxy-1,2,4-triazole | methanesulphonic acid chloride | 1-neo-hexyl-1,2,4-triazolyl-(3)-methanesulphonate | |
| 1-cyclopentyl-3-hydroxy-1,2,4-triazole | methanesulphonic acid chloride | 1-cyclopentyl-1,2,4-triazolyl-(3)-methanesulphonate | |
| 1-cyclohexyl-3-hydroxy-1,2,4-triazole | methanesulphonic acid chloride | 1-cyclohexyl-1,2,4-triazolyl-(3)-methanesulphonate | |
| 1-methyl-3-hydroxy-1,2,4-triazole | methanesulphonic acid chloride | 1-methyl-1,2,4-triazolyl-methanesulphonate | |
| 1,5-dimethyl-3-hydroxy-1,2,4-triazole | methanesulphonic acid chloride | 1,5-dimethyl-1,2,4-triazolyl-(3)-methanesulphonate | |
| 1,5-diethyl-3-hydroxy-1,2,4-triazole | methanesulphonic acid chloride | 1,5-diethyl-1,2,4-triazolyl-(3)-methanesulphonate | |
| 1-propyl-3-hydroxy-5-methyl-1,2,4-triazole | methanesulphonic acid chloride | 1-propyl-5-methyl-1,2,4-triazolyl-(3)-methanesulphonate | |
| 1-propyl-3-hydroxy-5-ethyl-1,2,4-triazole | methanesulphonic acid chloride | 1-propyl-5-ethyl-1,2,4-triazolyl-(3)-methanesulphonate | |
| 1-isopropyl-3-hydroxy-5-ethyl-1,2,4-triazole | methanesulphonic acid chloride | 1-isopropyl-5-ethyl-1,2,4-triazolyl-(3)-methanesulphonate | |
| 1,5-di-isopropyl-3-hydroxy-1,2,4-triazole | methanesulphonic acid chloride | 1,5-di-isopropyl-1,2,4-triazolyl-(3)-methanesulphonate | |
| 1-n-butyl-3-hydroxy-5-methyl-1,2,4-triazole | methanesulphonic acid chloride | 1-n-butyl-5-methyl-1,2,4-triazolyl-(3)-methanesulphonate | |
| 1-n-butyl-3-hydroxy-5-ethyl-1,2,4-triazole | methanesulphonic acid chloride | 1-n-butyl-5-ethyl-1,2,4-triazolyl-(3)-methanesulphonate | |
| 1-cyclopentyl-3-hydroxy-5-methyl-1,2,4-triazole | methanesulphonic acid chloride | 1-cyclopentyl-5-methyl-1,2,4-triazolyl-(3)-methanesulphonate | |
| 1-methyl-3-hydroxy-5-chloro-1,2,4-triazole | methanesulphonic acid chloride | 1-methyl-5-chloro-1,2,4-triazolyl-(3)-methanesulphonate | |
| 1-ethyl-3-hydroxy-5-chloro-1,2,4-triazole | methanesulphonic acid chloride | 1-ethyl-5-chloro-1,2,4-triazolyl-(3)-methanesulphonate | |
| 1-isopropyl-3-hydroxy-5-bromo-1,2,4-triazole | methanesulphonic acid chloride | 1-isopropyl-5-bromo-1,2,4-triazolyl-(3)-methanesulphonate | |
| 1-isopropyl-3-hydroxy-5-fluoro-1,2,4-triazole | methanesulphonic acid chloride | 1-isopropyl-5-fluoro-1,2,4-triazolyl-(3)-methanesulphonate | |
| 1-n-butyl-3-hydroxy-5-chloro-1,2,4-triazole | methanesulphonic acid chloride | 1-n-butyl-5-chloro-1,2,4-triazolyl-(3)-methanesulphonate | |
| 1-i-butyl-3-hydroxy-5-chloro-1,2,4-triazole | methanesulphonic acid chloride | 1-i-butyl-5-chloro-1,2,4-triazolyl-(3)-methanesulphonate | |
| 1-sec.-pentyl-3-hydroxy-5-chloro-1,2,4-triazole | methanesulphonic acid chloride | 1-sec.-pentyl-5-chloro-1,2,4-triazolyl-(3)-methanesulphonate | |
| 1-n-hexyl-3-hydroxy-5-chloro-1,2,4-triazole | methanesulphonic acid chloride | 1-n-hexyl-5-chloro-1,2,4-triazolyl-(3)-methanesulphonate | |
| 1-cyclopentyl-3-hydroxy-5-chloro-1,2,4-triazole | methanesulphonic acid chloride | 1-cyclopentyl-5-chloro-1,2,4-triazolyl-(3)-methanesulphonate | |
| 1-methyl-3-hydroxy-5-ethylthio-1,2,4-triazole | methanesulphonic acid chloride | 1-methyl-5-ethylthio-1,2,4-triazolyl-(3)-methanesulphonate | |
| 1-methyl-3-hydroxy-5-isopentylthio-1,2,4-triazole | methanesulphonic acid chloride | 1-methyl-5-isopentyl-thio-1,2,4-triazolyl-(3)-methanesulphonate | |
| 1-methyl-3-hydroxy-5-heptylthio-1,2,4-triazole | methanesulphonic acid chloride | 1-methyl-5-heptylthio-1,2,4-triazolyl-(3)-methanesulphonate | |
| 1-methyl-3-hydroxy-5-benzylthio-1,2,4-triazole | methanesulphonic acid choride | 1-methyl-5-benzylthio-1,2,4-triazolyl-(3)-methanesulphonate | |
| 1-methyl-3-hydroxy-5-benzylsulphonyl-1,2,4-triazole | methanesulphonic acid chloride | 1-methyl-5-benzylsulphonyl-1,2,4-triazolyl-(3)-methanesulphonate | |
| 1-methyl-3-hydroxy-5-ethylsulphonyl | methanesulphonic acid chloride | 1-methyl-5-ethylsulphonyl-1,2,4-triazolyl-(3)-methanesulphonate | |
| 1-ethyl-3-hydroxy-5- | methanesulphonic | 1-ethyl-5-propyl- | |

-continued

| Heterocycles | Sulphonic acid halide | Product | Physical data |
|---|---|---|---|
| propylthio-1,2,4-triazole | acid chloride | thio-1,2,4-triazolyl-(3)-methanesulphonate | |
| 1-ethyl-3-hydroxy-5-isopropyl-1,2,4-triazole | methanesulphonic acid chloride | 1-ethyl-5-isopropyl-1,2,4-triazolyl-(3)-methanesulphonate | |
| 1-propyl-3-hydroxy-5-ethylthio-1,2,4-triazole | methanesulphonic acid chloride | 1-propyl-5-ethylthio-1,2,4-triazolyl-(3)-methanesulphonate | |
| 1-iso-propyl-3-hydroxy-5-methyl-thio-1,2,4-triazole | methanesulphonic acid chloride | 1-isopropyl-5-methyl-thio-1,2,4-triazolyl-(3)-methanesulphonate | |
| 1-isopropyl-3-hydroxy-5-ispropylthio-1,2,4-triazole | methanesulphonic acid chloride | 1-isopropyl-5-isopropyl-thio-1,2,4-triazolyl-(3)-methanesulphonate | |
| 1-isopropyl-3-hydroxy-5-phenylthio-1,2,4-triazole | methanesulphonic acid chloride | 1-isopropyl-5-phenylthio-1,2,4-triazolyl-(3)-methanesulphonate | |
| 1-isopropyl-3-hydroxy-5-ethylsulphonyl-1,2,4-triazole | methanesulphonic acid chloride | 1-isopropyl-5-ethylsulphonyl-1,2,4-triazolyl-(3)-methanesulphonyl | |
| 1-n-butyl-3-hydroxy-5-ethylthio-1,2,4-triazole | methanesulphonic acid chloride | 1-n-butyl-5-ethylthio-1,2,4-triazolyl-(3)-methanesulphonate | |
| 1-sec.-butyl-3-hydroxy-5-methylthio-1,2,4-triazole | methanesulphonic acid chloride | 1-sec.-butyl-5-methylthio-1,2,4-triazolyl-(3)-methanesulphonate | |
| 1-sec.-butyl-3-hydroxy-5-ethylthio-1,2,4-triazole | methanesulphonic acid chloride | 1-sec.-butyl-5-ethylthio-1,2,4-triazolyl-(3)-methanesulphonate | |
| 1-cyclopentyl-3-hydroxy-5-methylthio-1,2,4-triazole | methanesulphonic acid chloride | 1-cyclopentyl-5-methylthio-1,2,4-triazolyl-(3)-methanesulphonate | |
| 1-cyclopentyl-3-hydroxy-5-ethylthio-1,2,4-triazole | methanesulphonic acid chloride | 1-cyclopentyl-5-ethylthio-1,2,4-triazolyl-(3)-methanesulphonate | |
| 1-isopropyl-3-hydroxy-5-methoxy-1,2,4-triazole | methanesulphonic acid chloride | 1-isopropyl-5-methoxy-1,2,4-triazolyl-(3)-methanesulphonate | |
| i-isopropyl-3-hydroxy-5-ethoxy-1,2,4-triazole | methanesulphonic acid chloride | 1-isopropyl-5-ethoxy-1,2,4-triazolyl-(3)-methanesulphonate | |
| 1-isopropyl-3-hydroxy-5-methylamino-1,2,4-triazole | methanesulphonic acid chloride | 1-isopropyl-5-methyl-amino-1,2,4-triazolyl-(3)-methanesulphonate | |
| 1-isopropyl-3-hydroxy-5-dimethylamino-1,2,4-triazole | methanesulphonic acid chloride | 1-isopropyl-5-dimethyl-amino-1,2,4-triazolyl-(3)-methanesulphonate | |
| 1-isopropyl-3-hydroxy-5-morpholino-1,2,4-triazole | methanesulphonic acid chloride | 1-isopropyl-5-morpholino-1,2,4-triazolyl-(3)-methanesulphonate | |
| 1-methyl-5-hydroxy-1,2,4-triazole | methanesulphonic acid chloride | 1-methyl-1,2,4-triazolyl-(5)-methanesulphonate | |
| 1,3-dimethyl-5-hydroxy-1,2,4-triazole | methanesulphonic acid chloride | 1,3-dimethyl-1,2,4-triazolyl-(5)-methanesulphonate | |
| 1-methyl-3-ethyl-5-hydroxy-1,2,4-triazole | methanesulphonic acid chloride | 1-methyl-3-ethyl-1,2,4-triazolyl-(5)-methane sulphonate | |
| 1-methyl-3-propyl-5-hydroxy-1,2,4-triazole | methanesulphonic acid chloride | 1-methyl-3-propyl-1,2,4-triazolyl-(5)-methanesulphonate | |
| 1-methyl-3-isopropyl-5-hydroxy-1,2,4-triazole | methanesulphonic acid chloride | 1-methyl-3-isopropyl-1,2,4-triazolyl-(5)-methanesulphonate | |
| 1-methyl-3-phenyl-5-hydroxy-1,2,4-triazole | methanesulphonic acid chloride | 1-methyl-3-phenyl-1,2,4-triazole-(5)-methanesulphonate | |
| 1-cyanoethyl-3-methyl-5-hydroxy-1,2,4-triazole | methanesulphonic acid chloride | 1-cyanoethyl-3-methyl-1,2,4-triazolyl-(5)-methanesulphonate | |
| 1-cyanoethyl-3-ethyl-5-hydroxy-1,2,4-triazole | methanesulphonic acid chloride | 1-cyanoethyl-3-ethyl-1,2,4-triazolyl-(5)-methanesulphonate | |
| 1-cyanoethyl-3-ispropyl-5-hydroxy-1,2,4-triazole | methanesulphonic acid chloride triazolyl-(5)- | 1-cyanoethyl-3-iso-propyl-1,2,4-methanesulphonate | |
| 1-phenyl-3-methyl-5-hydroxy-1,2,4-triazole | methanesulphonic acid chloride | 1-phenyl-3-methyl-1,2,4-triazolyl-(5)-methanesulphonate | |
| 1-phenyl-3-isopropyl-5-hydroxy-1,2,4-triazole | methanesulphonic acid chloride | 1-phenyl-3-isopropyl-1,2,4-triazolyl-(5)-methanesulphonate | |

-continued

| Heterocycles | Sulphonic acid halide | Product | Physical data |
|---|---|---|---|
| 1-phenyl-3-methylthio-5-hydroxy-1,2,4-triazole | methanesulphonic acid chloride | 1-phenyl-3-methlthio-1,2,4-triazolyl-(5)-methanesulphonate | |
| 1-phenyl-3-ethoxy-5-hydroxy-1,2,4-triazole | methanesulphonic acid chloride | 1-phenyl-3-ethoxy-1,2,4-triazolyl-(5)-methanesulphonate | |
| 1-methyl-3-phenoxy-5-hydroxy-1,2,4-triazole | methanesulphonic acid chloride | 1-methyl-3-phenoxy-1,2,4-triazolyl-(5)-methanesulphonate | |
| 1-methyl-3-ethoxy-5-hydroxy-1,2,4-triazole | methanesulphonic acid chloride | 1-methyl-3-ethoxy-1,2,4-triazolyl-(5)-methanesulphonate | |
| 1-(m-chlorophenyl)-3-hydroxy-1,2,4-triazole | methanesulphonic acid chloride | 1-(m-chlorophenyl)-1,2,4-triazolyl-(3)-methanesulphonate | |
| 1-(p-tolyl)-3-hydroxy-1,2,4-triazole | methanesulphonic acid chloride | 1-(o-tolyl)-1,2,4-triazolyl-(3)-methanesulphonate | |
| 1-(p-nitrophenyl)-3-hydroxy-1,2,4-triazole | methanesulphonic acid chloride | 1-(p-nitrophenyl-1,2,4-triazolyl-(3)-methanesulphonate | |
| 1-phenyl-5-methyl-3-hydroxy-1,2,4-triazole | methanesulphonic acid chloride | 1-phenyl-5-methyl-1,2,4-triazolyl-(3)-methanesulphonate | |
| 1-(3',5'-dichlorophenyl)-3-hydroxy-1,2,4-triazole | methanesulphonic acid chloride | 1-(3',5'-dichlorophenyl)-1,2,4-triazolyl-(3)-methanesulphonate | |
| 1-(3'-chloro-p-tolyl)-3-hydroxy-1,2,4-triazole | methanesulphonic acid chloride | 1-(3'-chloro-p-tolyl)-1,2,4-triazolyl-(3)-methanesulphonate | |
| 1-(3'-chlorophenyl)-5-ethyl-3-hydroxy-1,2,4-triazole | methanesulphonic acid chloride | 1-(3'-chlorophenyl)-5-ethyl-1,2,4-triazolyl-(3)-methanesulphonate | |
| 1-(3'-chlorophenyl)-5-propenyl-3-hydroxy-1,2,4-triazole | methanesulphonic acid chloride | 1-(3'-chlorophenyl)-5-propenyl-1,2,4-triazolyl-(3)-methanesulphonate | |
| 1-(3',5'-dichlorophenyl)-5-methyl-3-hydroxy-1,2,4-triazole | methanesulphonic acid chloride | 1-(3',5'-dichlorophenyl)-5-methyl-1,2,4-triazolyl-(3)-methanesulphonate | |
| 1-(m-trifluoromethylphenyl)-5-methyl-3-hydroxy-1,2,4-triazole | methanesulphonic acid chloride | 1-(m-trifluoromethylphenyl)-5-methyl-1,2,4-triazolyl-(3)-methanesulphonate | |
| 1-(4'-chloro-o-tolyl)-5-hydroxy-1,2,4-triazole | methanesulphonic acid chloride | 1-(4'-chloro-o-tolyl)-1,2,4-triazolyl-(3)-methanesulphonate | |
| 1-(p-fluorophenol)-3-hydroxy-1,2,4-triazole | methanesulphonic acid chloride | 1-(p-fluorophenyl)-1,2,4-triazolyl-(3)-methanesulphonate | |
| 1-(p-fluorophenyl)-5-methyl-3-hydroxy-1,2,4-triazole | methanesulphonic acid chloride | 1-(p-fluorophenyl)-5-methyl-1,2,4-triazolyl-(3)-methanesulphonate | |
| 1-phenyl-5-carbethoxy-3-hydroxy-1,2,4-triazole | methanesulphonic acid chloride | 1-phenyl-5-carbethoxy-1,2,4-triazolyl-(3)-methanesulphonate | |
| 1-isopropyl-3-hydroxy-1,2,4-triazole | ethanesulphonic acid chloride | 1-isopropyl-1,2,4-triazolyl-(3)-ethanesulphonate | |
| 1-isopropyl-3-hydroxy-1,2,4-triazole | n-propanesulphonic acid chloride | 1-isopropyl-1,2,4-triazolyl-(3)-n-propanesulphonate | |
| 1-isopropyl-3-hydroxy-1,2,4-triazole | iso-butanesulphonic acid chloride | 1-isopropyl-1,2,4-triazolyl-(3)-iso-butanesulphonate | |
| 1-ispropyl-3-hydroxy-1,2,4-triazole | n-hexanesulphonic acid chloride | 1-isopropyl-1,2,4-triazolyl-(3)-n-hexanesulphonate | |
| 1-isopropyl-3-hydroxy-1,2,4-triazole | 2-ethoxy-1-ethanesulphonic acid chloride | 1-isopropyl-1,2,4-triazolyl-(3)-2-ethoxy-1-ethanesulphonate | |
| 1-isopropyl-3-hydroxy-1,2,4-triazole | 2-octanesulphonic acid chloride | 1-isopropyl-1,2,4-triazolyl-(3)-2-octanesulphonate | |
| 1-isopropyl-3-hydroxy-1,2,4-triazole | chloromethanesulphonic acid chloride | 1-isopropyl-1,2,4-triazolyl-(3)-chloromethanesulphonate | |
| 1-isopropyl-3-hydroxy-1,2,4-triazole | 3-chloro-1-propanesulphonic acid chloride | 1-ispropyl-1,2,4-triazolyl-(3)-3-chloro-1-propenesulphonate | |
| 1-isopropyl-3-hydroxy-1,2,4-triazole | trifluoromethanesulphonic acid chloride | 1-isopropyl-1,2,4-triazolyl-(3)-trifluoromethanesulphonate | |
| 1-isopropyl-3-hydroxy-1,2,4-triazole | perfluoro-n-butanesulphonic acid chloride | 1-isopropyl-1,2,4-triazolyl-(3)-perfluoro-n-butane- | |

| Heterocycles | Sulphonic acid halide | -continued<br>Product | Physical data |
|---|---|---|---|
| 1-isopropyl-3-hydroxy-1,2,4-triazole | trichloromethanesulphonic acid chloride | sulphonate<br>1-isopropyl-1,2,4-triazolyl-(3)-trichloromethanesulphonate | |
| 1-isopropyl-3-hydroxy-1,2,4-triazole | ethylenesulphonic acid chloride | 1-isopropyl-1,2,4-triazolyl-(3)-ethylenesulphonate | |
| 5-phenyl-3-hydroxy-1,2,4-oxydiazole | methanesulphonic acid chloride | 5-phenyl-1,2,4-oxadiazolyl-(3)-methanesulphonate | |
| 5-(2-chlorophenyl)-3-hydroxy-1,2,4-oxadiazole | methanesulphonic acid chloride | 5-(2-chlorophenyl)-1,2,4-oxadiazolyl-(3)-methanesulphonate | |
| 5-(m-toluyl)-3-hydroxy-1,2,4-oxadiazole | methanesulphonic acid chloride | 5-(m-toluyl)-1,2,4-oxadiazolyl-(3)-methanesulphonate | |
| 5-methyl-3-hydroxy-1,2,4-oxadiazole | methanesulphonic acid chloride | 5-methyl-1,2,4-oxadiazolyl-(3)-methanesulphonate | |
| 5-tert.-butyl-3-hydroxy-1,2,4-oxadiazole | methanesulphonic acid chloride | 5-tert.-butyl-1,2,4-oxadiazolyl-(3)-methanesulphonate | |
| 5-chloromethyl-3-hydroxy-1,2,4-oxadiazole | methanesulphonic acid chloride | 5-chloromethyl-1,2,4-oxadiazolyl-(3)-methanesulphonate | |
| 5-n-pentyl-3-hydroxy-1,2,4-oxadiazole | methansulphonic acid chloride | 5-n-pentyl-1,2,4-oxadiazolyl-(3)-methanesulphonate | |
| 5-(3-chloroproyl)-3-hydroxy-1,2,4-oxadiazole | methanesulphonic acid chloride | 5-(3-chloropropyl)-1,2,4-oxadiazolyl-(3)-methanesulphonate | |
| 5-methylthiomethyl-3-hydroxy-1,2,4-oxadiazole | methanesulphonic acid chloride | 5-methylthiomethyl-1,2,4-oxadiazolyl-(3)-methanesulphonate | |
| 5-phenoxymethyl-3-hydroxy-1,2,4-oxadiazole | methanesulphonic acid chloride | 5-phenoxymethyl-1,2,4-oxadiazolyl-(3)-methanesulphonate | |
| 5-benzyl-3-hydroxy-1,2,4-oxadiazole | methanesulphonic acid chloride | 5-benzyl-1,2,4-oxadiazolyl-(3)-methanesulphonate | |
| 5-(2-furyl)-3-hydroxy-1,2,4-oxadiazole | methanesulphonic acid chloride | 5-(2-furyl)-1,2,4-oxadiazolyl-(3)-methanesulphonate | |
| 3-phenyl-5-hydroxy-1,2,4-oxadiazole | methanesulphonic acid chloride | 3-phenyl-1,2,4-oxadiazolyl-(5)-methanesulphonate | |
| 3-methyl-5-hydroxy-1,2,4-oxadiazle | methanesulphonic acid chloride | 3-methyl-1,2,4-oxadiazolyl-(5)-methanesulphonate | |
| 3-chloromethyl-5-hydroxy-1,2,4-oxadiazole | methanesulphonic acid chloride | 3-chloromethyl-1,2,4-oxadiazolyl-(5)-methanesulphonate | |
| 3-ethyl-5-hydroxy-1,2,4-oxadiazole | methanesulphonic acid chloride | 3-ethyl-1,2,4-oxadiazolyl-(5)-methanesulphonate | |
| 3-tert.-butyl-5-hydroxy-1,2,4-oxadiazole | methanesulphonic acid chloride | 3-tert.-butyl-1,2,4-oxadiazolyl-(5)-methanesulphonate | |
| 3-isopropyl-5-hydroxy-1,2,4-oxadiazole | methanesulphonic acid chloride | 3-isopropyl-1,2,4-oxadiazolyl-(5)-methanesulphonate | |
| 3-n-butoxy-5-hydroxy-1,2,4-oxadiazole | methanesulphonic acid chloride | 3-n-butoxy-1,2,4-oxadiazolyl-(5)-methanesulphonate | |
| 5-methyl-3-hydroxy-1,2,4-thiadiazole | methanesulphonic acid chloride | 5-methyl-1,2,4-thiadiazolyl-(3)-methanesulphonate | |
| 3-methyl-5-hydroxy-1,2,4-thiadiazole | methanesulphonic acid chloride | 3-methyl-1,2,4-thiazolyl-(5)-methanesulphonate | |
| 3-ispropyl-5-hydroxy-1,2,4-thiadiazole | methanesulphonic acid chloride | 3-isopropyl-1,2,4-thiadiazolyl-(5)-methanesulphonate | |
| 3-hydroxy-1,2,5-thiadiazole | methanesulphonic acid chloride | 1,2,5-thiadiazolyl-(3)-methanesulphonate | |
| 4-methyl-3-hydroxy-1,2,5-thiadiazole | methanesulphonic acid chloride | 4-methyl-1,2,5-thiadiazolyl-(3)-methanesulphonate | |
| 4-isopropyl-3-hydroxy-1,2,5-thiadiazole | methanesulphonic acid chloride | 4-isopropyl-1,2,5-thiadiazolyl-(3)-methanesulphonate | |
| 4-chloro-3-hydroxy-1,2,5-thiadiazole | methanesulphonic acid chloride | 4-chloro-1,2,5-thiadiazolyl-(3)-methanesulphonate | |
| 4-methoxy-3-hydroxy-1,2,5-thiadiazole | methanesulphonic acid chloride | 4-methoxy-1,2,5-thiadiazolyl-(3)-methanesulphonate | |
| 4-methylthio-3-hydroxy-1,2,5-thiadiazole | methanesulphonic acid chloride | 4-methylthio-1,2,5-thiadiazolyl-(3)-methanesulphonate | |

-continued

| Heterocycles | Sulphonic acid halide | Product | Physical data |
| --- | --- | --- | --- |
| 4-isopropoxy-3-hydroxy-1,2,5-thiadiazole | methanesulphonic acid chloride | 4-isopropoxy-1,2,5-thiadiazolyl-(3)-methanesulphonate | |
| 4-phenoxy-3-hydroxy-1,2,5-thiadiazole | methanesulphonic acid chloride | 4-phenoxy-1,2,5-thiadiazolyl-(3)-methanesulphonate | |
| 4-phenyl-3-hydroxy-1,2,5-thiadiazole | methanesulphonic acid chloride | 4-phenyl-1,2,5-thiadiazolyl-(3)-methanesulphonate | |
| 1-oxy-2-phenyl-4-hydroxy-1,2,3-triazole | methanesulphonic acid chloride | 1-oxy-2-phenyl-1,2,3-triazolyl-(4)-methanesulphonate | |
| 2-methyl-4-hydroxy-1,2,3-triazole | methanesulphonic acid chloride | 2-methyl-1,2,3-triazolyl-(4)-methanesulphonate | |
| 2-isopropyl-4-hydroxy-1,2,3-triazole | methanesulphonic acid chloride | 2-isopropyl-1,2,3-triazolyl-(4)-methanesulphonate | |
| 1-phenyl-4-methyl-5-hydroxy-1,2,3-triazole | methanesulphonic acid chloride | 1-phenyl-4-methyl-1,2,3-triazolyl-(5)-methanesulphonate | |
| 3-hydroxy-1,2,3-benztriazole | methanesulphonic acid chloride | 1,2,3-benztriazolyl-(3)-methanesulphonate | |

EXAMPLE 2

A. Insecticidal stomach poison action

Cotton and potato plants were sprayed with a 0.05% aqueous active-substance emulsion (obtained from a 10% emulsifiable concentrate).

After the drying of the obtained coating, *Spodoptera litoralis* or *Heliothis virescens* larvae $L_3$ were placed onto the cotton plants, and Colorada beetle larvae (*Leptinotarsa decemlineata*) onto the potato plants. The test was carried out at 24°C with 60% relative humidity.

The compounds according to Example 1 exhibited in the above test a good insecticidal stomach poison action against *Spodoptera litoralis*, *Heliothis* and *Leptinotarsa decemlineata* larvae.

B. Systemic insecticidal action

In order to determine the systemic action, rooted bean plants (*Vicia faba*) were placed into a 0.01% aqueous active-substance solution (obtained from a 10% emulsifiable concentrate). After a period of 24 hours, bean aphids (*Aphis fabae*) were placed onto the parts of the plants above the soil. The insects were protected by a special device from the effects of contact and of gas. The test was carried out at 24°C with 70% relative humidity.

In the above test, the compounds according to Example 1 exhibited a systemic action against *Aphis fabae*.

EXAMPLE 3

Action against *Chilo suppressalis*

Rice plants of the type Caloro were planted, 6 plants per pot, in plastic pots having a top diameter of 17 cm, and grown to a height of ca. 60 cm. Infestation with *Chilo suppressalis* larvae ($L_1$; 3–4 mm long) was carried out 2 days after application of the active substance in granular form (amount applied = 8 kg of active substance per hectare) to the paddy water. The evaluation of the insecticidal action was made 10 days after application of the granules.

The compounds according to Example 1 were effective against *Chilo suppressalis* in the above test.

EXAMPLE 4

Sterilised compost soil was homogeneously mixed with a wettable powder containing 25% of active substance, so that the resulting amount applied was 8 kg of active substance per hectare. Young zucchetti plants (*Cucumis pepo*) were potted in plastic pots containing the treated soil (three plants per pot of 7 cm diameter). The pots were infested immediately afterwards with 5 *Aulacophora femoralis* larvae or 5 *Pachmoda* larvae or 5 *Chortophila* larvae per pot. An examination was made 4, 8, 16 and 32 days after infestation. In the case of 80–100% destruction of the larvae on the first examination, a new infestation with 5 larvae in each case was effected in the same sample of soil but with 3 new zucchetti plants. Where the action was less than 80%, the surviving insects remained in the test soil until the following control examination. If a substance with an effective applied amount of 8 kg/hectare produced 100% destruction, then a subsequent test was made using 4 and 2 kg of active substance/hectare, respectively.

The compounds according to Example 1 were effective in the above test against *Aulacophora femoralis* larvae, *Pachmoda* larvae and *Chortophila* larvae.

EXAMPLE 5

Action against ticks

A. *Rhipicephalus bursa*

In each case, 5 adult ticks or 50 tick larvae were placed into a small glass test tube, and the test tubes then immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks, and in the case of the larvae after 2 days. There were two repeats for each test.

B. *Boophilus microplus* (larvae)

With a dilution series analogous to that in Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

EXAMPLE 6

Acaricidal action

*Phaseolus vulgaris* (plants) were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no running off of the spray liquor. An assessment was made after 2 to 7 days, by examination under a binocular, of the living and of the dead larvae, adults and eggs, and the results expressed in percentages. The treated plants were kept during the "holding time" in greenhouse compartments at 25°C.

The compounds according to Example 1 were effective in the above test against adults, larvae and eggs of *Tetranychus urticae*.

EXAMPLE 7

Action against soil nematodes

In order to test the action against soil nematodes the active substances were added, in the concentration stated in each case, to soil infested with root-gall-nematodes (*Meloidogyne arenaria*), and the whole intimately mixed. In the one test series, tomato seedlings were planted immediately afterwards in the thus prepared soil, and in the other test series tomatoes were planted after a waiting time of 8 days.

For an assessment of the nematicidal action, the galls present on the roots were counted 28 days after planting and sowing, respectively.

Active substances according to Example 1 exhibited in this test a good action against *Meloidogyne arenaria*.

EXAMPLE 8

Fungicidal action

Action against *Erysiphe chichoracearum* on *Cucumis sativus*

Young *Cucumis sativus* plants were sprayed with a 0.1% suspension of the active substance formulated as a wettable powder; after drying of the applied coating, the said plants were sprayed with a spore suspension of the fungus. After 8 days in a greenhouse at about 23°C, the plants were examined in order to determine the degree of infestation (percentage of the leaf surface covered by a film of mycelium) on the infected and treated leaves compared with that on the infected but untreated control specimens.

What we claim is:

1. A sulphonic acid ester of the formula $$R_1 - SO_2 - O - R_2$$

wherein
  $R_1$ represents $C_1$–$C_6$ alkyl or $C_2$–$C_5$ alkenyl optionally substituted by halogen, lower alkoxy or lower alkylthio; and
  $R_2$ represents 1,2,3-triazolyl(4), 1,2,3-triazolyl(5), 1,2,4-triazolyl(5) or 1,2,4-triazolyl(3) optionally substituted by halogen; alkoxy, alkylthio, alkylsulphinyl, alkylsulphonyl, alkylthioalkyl, haloalkyl or alkoxyalkyl, each having lower alkyl groups; alkenyl, alkenyloxy or alkenylthio each having 2–5 carbon atoms; amino, mono-(lower)alkylamino or di-(lower)alkylamino; carbamoyl; carb-(lower)alkoxy; nitro; cyano; or phenyl, phenylthio, phenylsulphinyl, phenylsulphonyl, benzyl, benzylthio, benzylsulphinyl, benzylsulphonyl, 1-phenethyl, 2-phenethyl, diphenylmethyl or $C_5$–$C_6$ cycloalkyl, optionally substituted by halogen, lower alkyl, lower haloalkyl, lower alkoxy, lower alkylthio or nitro.

2. The sulphonic acid ester according to claim 1 wherein $R_1$ represents unsubstituted $C_1$–$C_6$ alkyl, $C_1$–$C_6$ alkyl substituted by fluorine or chlorine, or 3,3,3-trichloropropenyl(1), and $R_2$ represents 1,2,4-triazolyl(3) optionally substituted as defined in claim 1.

3. Sulphonic acid ester according to claim 2 of the formula

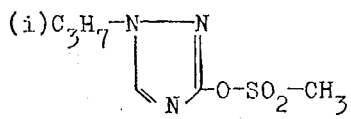

4. Sulphonic acid ester according to claim 2 of the formula

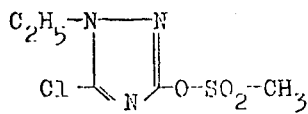

5. Sulphonic acid ester according to claim 2 of the formula

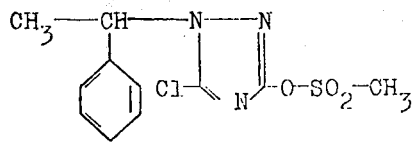

6. Sulphonic acid ester according to claim 2 of the formula

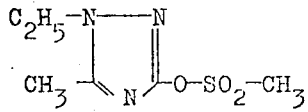

7. Sulphonic acid ester according to claim 2 of the formula

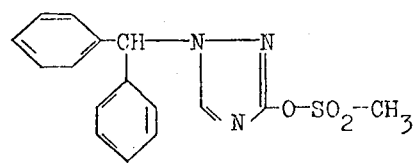

8. Sulphonic acid ester according to claim 2 of the formula

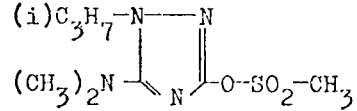

9. Sulphonic acid ester according to claim 2 of the formula
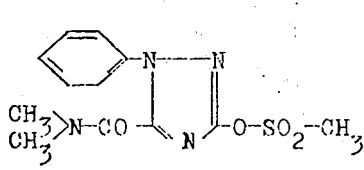
10. Sulphonic acid ester according to claim 2 of the formula
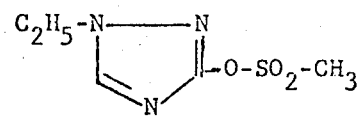
11. Sulphonic acid ester according to claim 2 of the formula
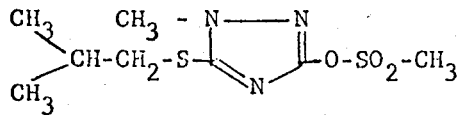
* * * * *